United States Patent [19]

Kesten

[11] Patent Number: 4,567,033

[45] Date of Patent: Jan. 28, 1986

[54] LOW-ENERGY METHOD FOR FREEING CHEMICALLY BOUND HYDROGEN

[75] Inventor: Arthur S. Kesten, West Hartford, Conn.

[73] Assignee: United Technologies Corporation, Hartford, Conn.

[21] Appl. No.: 664,825

[22] Filed: Oct. 25, 1984

[51] Int. Cl.[4] .............................................. C01B 13/00
[52] U.S. Cl. .................................. 423/648 R; 423/650; 585/660; 585/910
[58] Field of Search ........................... 423/648 R, 650; 585/660, 910, 911

[56] References Cited

U.S. PATENT DOCUMENTS

| 3,186,872 | 6/1965 | Ewing | 136/86 |
| 3,544,376 | 12/1970 | Connor, Jr. et al. | 136/86 |
| 3,975,913 | 8/1976 | Erickson | 60/645 |
| 4,200,682 | 4/1980 | Sederquist | 429/17 |
| 4,326,013 | 4/1982 | Jacobi et al. | 429/20 |
| 4,352,863 | 10/1982 | Maru | 429/17 |
| 4,476,918 | 10/1984 | Kesten | 422/190 |
| 4,478,814 | 10/1984 | Kesten et al. | 423/648 R |

*Primary Examiner*—John Doll
*Assistant Examiner*—Wayne A. Langel
*Attorney, Agent, or Firm*—A. Dean Olson

[57] ABSTRACT

A method for reducing the energy required in a dehydrogenation reaction particularly adapted to methods for transporting and storing thermal energy. The equilibrium of a hydrogenation-dehydrogenation equilibrium reaction system is shifted by removing at least a portion of the generated equilibrium reaction hydrogen and reacting the removed hydrogen with oxygen to produce water and heat and adding the produced water and heat into the equilibrium reaction system. This method has particular use in hydrogenation-dehydrogenation equilibrium reaction systems useful for transporting and storing thermal energy.

9 Claims, 1 Drawing Figure

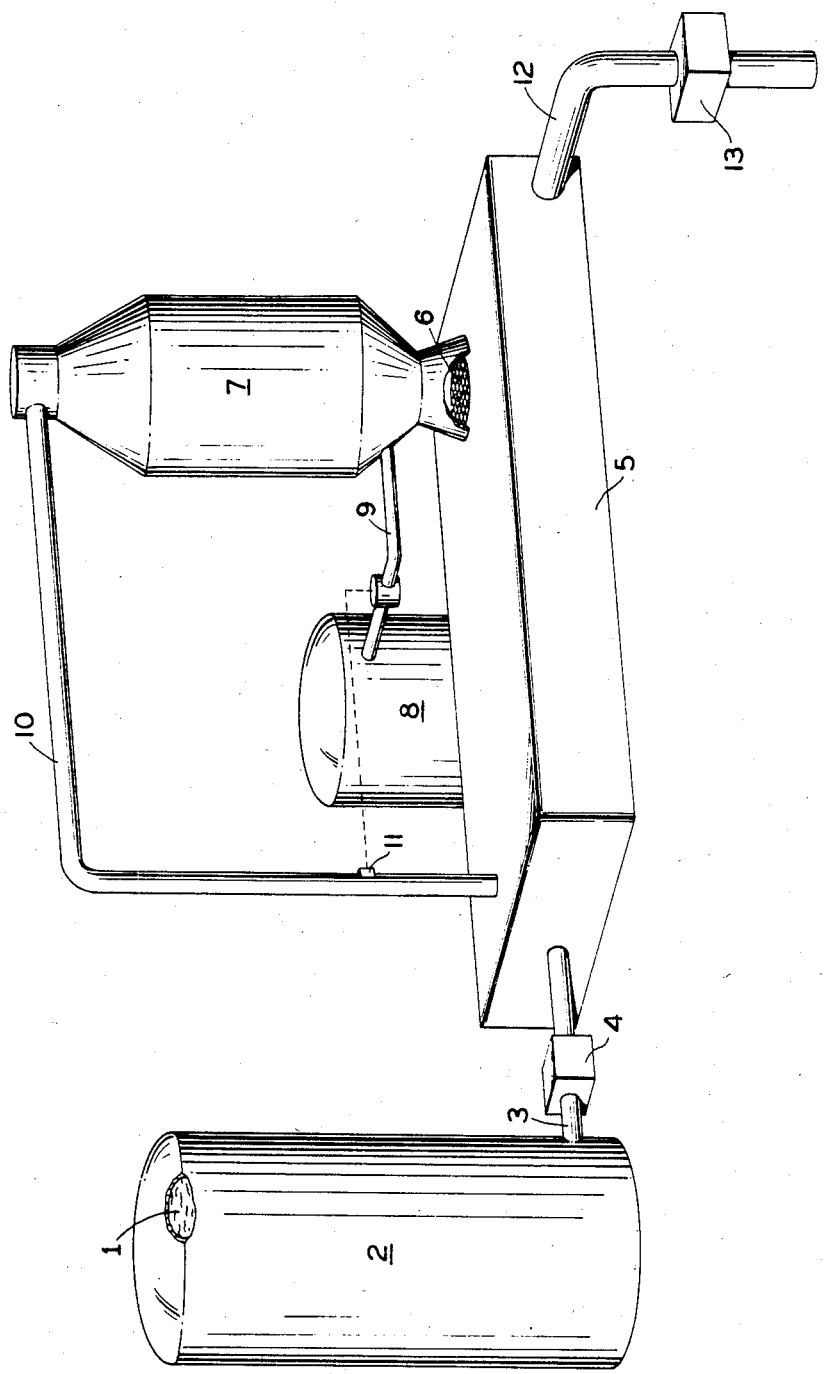

LOW-ENERGY METHOD FOR FREEING CHEMICALLY BOUND HYDROGENCL CROSS-REFERENCE TO RELATED APPLICATION

Attention is directed to commonly assigned, copending application Ser. No. 392,441 filed June 28, 1982, now U.S. Pat. No. 4,476,918, which discloses dehydrogenation processes, the disclosure of which is incorporated by reference.

DESCRIPTION

1. Technical Field

The present invention relates to dehydrogenation processes particularly adapted for use in a chemical heat pipe/storage system.

2. Background Art

Heat pipes have been especially useful in efficient transport of thermal energy between a thermal source and a thermal sink or load over short distances. However, typical vaporization/condensation heat pipes may experience significant radiation, convection and conduction losses to the environment when the transport path is relatively long, i.e., greater than 10 feet. To accomplish efficient transport over longer distances, resort has been made to reversible chemical heat pipe systems in which reactant(s) undergo an endothermic chemical reaction at the heat source and a second exothermic chemical reaction at the heat sink. This reduces the potential for thermal loss from the system as the reactant(s) and/or reaction products may be transported at temperatures similar to that of the environment.

Inherent to the concept of a chemical heat pump is the idea of energy storage. This may be visualized as a reversible chemical reaction where the products of the first endothermic reaction are stored instead of being transported. The development of a safe, reliable, efficient means of energy storage in the form of hydrogen is an important part of the U.S. energy program. Both compressed gas storage and cryogenic storage require large expenditures of energy making them unattractive. Various other advanced means of hydrogen storage such as the metal hydrides, cryoadsorption on activated charcoal, and the use of hollow glass microspheres which become permeable to hydrogen at high temperatures have all shown promise, but generally have failed to live up to early expectations. In contrast, the reversible liquid hydrogen storage alternatives have received little attention.

One such reaction is the hydrogenation of any of several aromatic hydrocarbons to produce the corresponding cycloparaffins. Note commonly assigned U.S. Pat. No. 4,346,752, the disclosure of which is incorporated by reference. However, there is room for improvement even to this system. For instance, relatively large amounts of energy are usually required for the dehydrogenation reaction. From the standpoint of both cost and safety it would be beneficial if the elevated temperatures that must be supplied could be eliminated.

Accordingly, what is needed in this art is a method of reducing the energy required for dehydrogenation in a hydrogenation-dehydrogenation equilibrium reaction system particularly adapted for use in a chemical heat pipe/storage system.

DISCLOSURE OF INVENTION

This disclosure is directed to a low energy method for freeing chemically bound hydrogen. In an innovative fashion the energy required for dehydrogenation has been reduced resulting in energy savings and increased safety.

One aspect of this invention is a method for reducing the energy required of a dehydrogenation reaction by shifting the equilibrium of the hydrogenation-dehydrogenation equilibrium reaction system. Some of the hydrogen generated by dehydrogenation is removed from the equilibrium reaction system through a membrane. The hydrogen that was removed is reacted with oxygen to produce water and heat, both of which are injected into the equilibrium reaction system. The reduced energy is a result of the removal of hydrogen and addition of heat to the equilibrium reaction system.

Another aspect of this invention is a method of storing, transporting, and releasing hydrogen fuel utilizing a cyclohexane or methylcyclohexane hydrogenation-dehydrogenation equilibrium reaction system. Some of the hydrogen generated by dehydrogenation of the cyclohexane or methylcyclohexane is removed from the equilibrium reaction system through a membrane. The hydrogen that was removed is reacted with oxygen to produce water and heat, which are both injected into the equilibrium reaction system. This results in energy savings through the removal of hydrogen and addition of heat to the equilibrium reaction system.

This discovery aids the advancement of energy storage and transfer technology through valuable low-energy dehydrogenation processes. These processes are most efficient as they add heat in the form of hot water directly to the reaction chamber, thus avoiding the losses associated with heat exchange across surfaces. The reduction in energy supplied is a significant step towards an economically viable liquid hydrogen energy system. Beyond its use in hydrogen storage and transfer applications this process can be advantageously utilized in any dehydrogenation process, i.e., the dehydrogenation of butane to 1,3 butadiene.

Other features and advantages will be apparent from the specification and claims and from the accompanying drawings illustrating an embodiment of the invention.

BRIEF DESCRIPTION OF DRAWING

The FIGURE is a generalized schematical diagram of the equilibrium-shifted dehydrogenation process of this invention.

BEST MODE FOR CARRYING OUT THE INVENTION

Referring to the drawings there is illustrated in the FIGURE a dehydrogenation reaction system that is generally conventional in the art. This low temperature dehydrogenation process will work with many equilibrium systems in which water is inert, preferably a cyclohexane-benzene or methylcyclohexanetoluene hydrogenation-dehydrogenation reaction system. Emperically this can be shown as

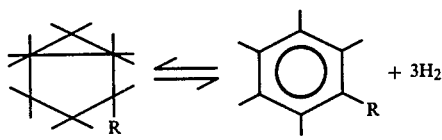

where R can be a hydrogen or methyl radical. Hydrogenated reactant 1 flows from a pressurized source 2 through a conduit 3 where its temperature is raised by a heater 4. The heater is generally only necessary to initiate the dehydrogenation process as once begun, the system's reactants themselves provide the energy for dehydrogenation. Next, the hydrogenated reactant 1 flows into a dehydrogenation reactor vessel 5.

In reactor vessel 5 the hydrogenated reactant undergoes a dehydrogenation reaction, preferably catalytically, as part of a hydrogenation-dehydrogenation equilibrium reaction system. It is especially preferred that the catalyst be a noble metal catalyst such as platinum. A portion of the product $H_2$ is removed from reactor vessel 5 through a membrane 6, preferably a palladium membrane. Membranes other than palladium will typically result in a less efficient system as some of the hydrocarbon gases will be lost from the system. The amount of $H_2$ removed can vary. Virtually any removal of $H_2$ will result in shifting the reaction equilibrium so that the dehydrogenation reaction can proceed with a reduced energy supply. In addition, the removed $H_2$ is oxidized to form heat and water which are both added to the dehydrogenation reactor vessel 5. Thus the preferred amount of hydrogen removed is just enough so that the shift in reaction equilibrium from the combination of, the $H_2$ removal and the addition of heated water exactly equal the heat required to effect dehydrogenation in reactor 5. This is about 25-30% (e.g. by weight) of the $H_2$ present in the equilibrium reaction system for temperatures between room temperature and 316° C. This can be achieved by conventional means through appropriate choice of membane thickness as the membrane thickness determines the permeation rate. The $H_2$ flows through membrane 6 into oxidation reactor vessel 7. A supply of pressurized oxygen 8 flows through conduit 9 into oxidation reactor vessel 7. Any supply of pressurized "free" oxygen will suffice such as is conventionally available (i.e., commercial grade, 99% purity). It will be understood by those skilled in the art that any source of oxygen, for example air (80% nitrogen, 20% oxygen) will serve as an acceptable substitute for free oxygen if any other gases present in significant amounts (e.g. argon) are chemically inert to this dehydrogenation reaction system.

One consideration in the choice of oxygen source is the comparative energy cost to the system. For instance, the use of air eliminates the energy cost associated with obtaining free oxygen. Also, the addition of an inert gas (e.g. nitrogen) into the system shifts the equilibrium to the right reducing the energy required to be supplied for dehydrogenation. Note copending application Ser. No. 392,441 filed June 28, 1982. That application teaches the shifting of equilibrium by the addition of an inert diluent, a requirement being an increase in volume in order to maintain a constant pressure. However, the utilization of air as an oxygen source has an inherently large energy cost in that the system heats nitrogen to no advantage. In addition the use of air ultimately requires a system to separate the other gases from hydrogen.

In oxidation reactor vessel 7 the hydrogen is oxidized, preferably catalytically. Emperically this can be shown as $2H_2 + O_2 \rightleftharpoons 2H_2O + Heat$. An especially preferred method is to catalyze the combustion with platinum catalysts. After combustion, the product stream (water, heat, unreacted $H_2$) flows out of reaction chamber 7 through conduit 10 past oxygen sensor 11. Any oxygen sensor conventional to the art, including electrolytic or infrared sensors, will suffice. The oxygen sensor 11 is connected to the oxygen supply 8 and as the product stream flows by the sensor it is used to regulate the flow oxygen to ensure that no significant oxygen ends up in the product stream. Oxygen in the product stream would eventually "poison" the catalysts used downstream in the equilibrium reaction system.

The product stream flows through conduit 10 and is added to the equilibrium reaction system in dehydrogenation reactor vessel 5. The addition of the product stream, to the equilibrium reaction system, adds heat directly to the dehydrogenation gas stream in the form of the hot reaction product water. The dehydrogenation product stream exits from the dehydrogenation reactor vessel 5 through conduit 12 and is separated into its components. The water and dehydrogenated product are condensed out by cooling apparatus 13 and if they are immiscible, like water and toluene, they are easily separated. The hydrogen may be separated from any other gases present, i.e., nitrogen by conventional means such as membranes.

In accordance with the present invention the equilibrium of the hydrogenation-dehydrogenation equilibrium reaction system is shifted to allow dehydrogenation to occur at a reduced energy level. This is accomplished by hydrogen removal from and water and heat addition to the equilibrium reaction system. For an understanding of how these two actions achieve dehydrogenation at a reduced temperature, consideration should be given to the following description.

The LeChatlier Principle states that whenever an external stress is imposed upon a system in equilibrium, the system reacts to the stress in such a way as to minimize its effect. As applied in this disclosure the decrease in concentration of $H_2$ makes the dehydrogenation the favored reaction of the hydrogenation-dehydrogenation equilibrium as the system attempts to replace some of the removed $H_2$. The addition of the heat also favors the dehydrogenation reaction (the energy absorbing reaction) as the system attempts to attain its initial temperature. It should be noted that although inert water vapor is added to the system there is no effect as the number of moles of water vapor added exactly equals the number of moles of hydrogen removed, keeping the system at constant pressure and volume.

EXAMPLE

The conventional dehydrogenation of methylcyclohexane to produce toluene at 316° C. requires that 53 kilo calories/mole of toluene be supplied for continual operation.

In contrast using this low energy method the dehydrogenation of methylcyclohexane to produce toluene at 316° C. requires no additional input of energy once start-up has been achieved. This is achieved when about 29% of the hydrogen is removed and combusted with oxygen to form heat and water which are added to the system.

This discovery can be utilized advantageously in a variety of ways. Any dehydrogenation reaction is a potential candidate for this system. However, it is generally limited to those equilibrium reactions where the components are inert to water vapor, such as the dehydrogenation of alkanes to produce olefins. For example the dehydrogenation of butane to 1,3 butadiene, which is the basis for the large volume production of synthetic rubber, would benefit from reduced energy costs. This discovery can also be utilized in a dehydrogenation reaction that is part of a chemical heat pipe or energy storage system (such as is described in the Background Art section) where energy is transferred or stored in the form of a liquid hydrogen "hydride".

The discovery lowers the energy required for dehydrogenation in a most efficient manner. The addition of heat in the form of hot water is added directly into the reaction chamber, thus avoiding the losses associated with heat exchange across surfaces. In addition the energy cost of obtaining that heat, i.e., free oxygen, is much less than the energy obtained from the combustion of hydrogen to produce water. Thus, the addition of only a supply of oxygen and a simple apparatus transforms a dangerous high energy reaction into a safe low energy reaction. This transformation has made possible a wide variety of uses for dehydrogenations.

In the chemical industry it makes possible certain dehydrogenations, that because of high or unsafe energy requirements, could not be utilized. This system can also be utilized in energy storage and/or transfer. In the energy field the reduction in energy for dehydrogenation reactions is a significant step towards the commercialization of liquid "hydride" hydrogen storage and transfer. This is important because liquid cycloparaffins although analogous to metal hydrides have significant advantages. For instance, the liquid hydrides have the great advantage of permitting the dehydrogenation reaction to proceed in a relatively small isolated reactor. This feature reduces the effective thermal mass of the system to that of the reactor plus a regeneration heat exchange element, irrespective of the volume of hydrogen storage elsewhere in the system. Also since the hydrogenation or dehydrogenation reactions do not occur in the absence of a suitable catalyst, the liquids can be stored in conventional (e.g. gasoline) storage facilities.

Although this invention has been shown and described with respect to detailed embodiments thereof, it will be understood by those skilled in the art that various changes in form and detail thereof may be made without departing from the spirit and scope of the claimed invention.

I claim:

1. A method for reducing the energy required for a dehydrogenation reaction by shifting the equilibrium of the hydrogenation-dehydrogenation equilibrium reaction system comprising:
   (a) removing at least a portion of the generated equilibrium reaction hydrogen through a membrane;
   (b) reacting the removed hydrogen with oxygen to produce water and heat; and
   (c) adding substantially all the produced water and heat into the equilibrium reaction system.

2. The method of claim 1 wherein the reaction system is selected from the group consisting of cyclohexane-benzene and methylcyclohexane-toluene.

3. The method as recited in claim 1 wherein the hydrogen is removed through a palladium membrane.

4. The method as recited in claim 1 wherein 25–30% of the hydrogen is removed.

5. The method for reducing the reaction temperature of a dehydrogenation reaction recited in claim 1 wherein the hydrogen and oxygen are reacted in the presence of platinum catalysts.

6. A method of storing, transporting and releasing hydrogen fuel utilizing a cyclohexane or methylcyclohexane hydrogenation-dehydrogenation equilibrium reaction system wherein the improvement comprises:
   (a) removing at least a portion of the generated equilibrium reaction hydrogen through a membrane;
   (b) reacting the removed hydrogen with oxygen to produce water and heat; and
   (c) adding substantially all the produced water and heat into the equilibrium reaction system.

7. The improved method of storing, transporting and releasing hydrogen fuel as recited in claim 6 wherein the hydrogen is removed through a palladium membrane.

8. The improved method of storing, transporting and releasing hydrogen fuel as recited in claim 6 wherein 25–30% of the hydrogen is removed.

9. The improved method of storing, transporting and releasing hydrogen fuel as recited in claim 6 wherein the hydrogen and oxygen are reacted in the presence of platinum catalysts.

* * * * *